(12) United States Patent
Rigo et al.

(10) Patent No.: US 10,538,763 B2
(45) Date of Patent: Jan. 21, 2020

(54) COMPOUNDS AND METHODS FOR MODULATION OF DUX4

(71) Applicants: Ionis Pharmaceuticals, Inc., Carlsbad, CA (US); Fred Hutchinson Cancer Research Center, Seattle, WA (US)

(72) Inventors: Frank Rigo, Carlsbad, CA (US); Stephen J. Tapscott, Seattle, WA (US)

(73) Assignees: Ionis Pharmaceuticals, Inc., Carlsbad, CA (US); Fred Hutchinson Cancer Research Center, Seattle, WA (US)

( * ) Notice: Subject to any disclaimer, the term of this patent is extended or adjusted under 35 U.S.C. 154(b) by 0 days.

(21) Appl. No.: 15/540,903

(22) PCT Filed: Jan. 15, 2016

(86) PCT No.: PCT/US2016/013649
§ 371 (c)(1),
(2) Date: Jun. 29, 2017

(87) PCT Pub. No.: WO2016/115490
PCT Pub. Date: Jul. 21, 2016

(65) Prior Publication Data
US 2018/0273942 A1  Sep. 27, 2018

Related U.S. Application Data

(60) Provisional application No. 62/104,610, filed on Jan. 16, 2015.

(51) Int. Cl.
*C12N 15/113* (2010.01)
*A61P 21/00* (2006.01)

(52) U.S. Cl.
CPC .......... *C12N 15/113* (2013.01); *A61P 21/00* (2018.01); *C12N 2310/14* (2013.01); *C12N 2310/315* (2013.01); *C12N 2310/32* (2013.01); *C12N 2310/321* (2013.01); *C12N 2310/351* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,185,444 A | 12/1993 | Summerton et al. |
| 5,276,019 A | 1/1994 | Cohen et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |

(Continued)

FOREIGN PATENT DOCUMENTS

| | | |
|---|---|---|
| WO | WO 2013/120038 | 8/2013 |
| WO | WO 2014/071340 | 5/2014 |

OTHER PUBLICATIONS

Ansseau et al., "Antisense strategies against DUX4 as a therapeutic approach for FSHD" P. Belg. Roy. Acad. Med. (2014) 3:194-204.

(Continued)

*Primary Examiner* — J. E. Angell
(74) *Attorney, Agent, or Firm* — McNeill Baur PLLC

(57) ABSTRACT

The present disclosure pertains generally to double-stranded small interfering RNAs that modulate gene expression for use in research, diagnostics, and/or therapeutics. In certain embodiments, the present disclosure provides double-stranded small interfering RNAs that modulate DUX4 gene expression. In certain embodiments, the present disclosure provides methods of inhibiting DUX4 gene expression by contacting a cell with double-stranded small interfering RNAs.

17 Claims, No Drawings

Specification includes a Sequence Listing.

(56) References Cited

U.S. PATENT DOCUMENTS

| | | |
|---|---|---|
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Burh et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Burh et al. |
| 5,801,154 A | 9/1998 | Baracchini et al. |
| 5,808,027 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'O |
| 6,005,087 A | 12/1999 | Cook et al. |
| 6,005,096 A | 12/1999 | Matteucci et al. |
| 6,166,199 A | 12/2000 | Cook et al. |
| 6,300,319 B1 | 10/2001 | Manoharan |
| 6,426,220 B1 | 7/2002 | Bennett et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,660,720 B2 | 12/2003 | Manoharan |
| 6,770,748 B2 | 8/2004 | Imanishi et al. |
| 6,846,922 B1 | 1/2005 | Manoharan et al. |
| 7,015,315 B1 | 3/2006 | Cook et al. |
| 7,053,207 B2 | 5/2006 | Wengel et al. |
| 7,101,993 B1 | 9/2006 | Cook et al. |
| 7,250,496 B2 | 7/2007 | Bentwich et al. |
| 7,262,177 B2 | 8/2007 | Ts'o et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,666,854 B2 | 2/2010 | Seth et al. |
| 7,691,997 B2 * | 4/2010 | Khvorova ............ A61K 31/713 536/24.5 |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,875,733 B2 | 1/2011 | Bhat et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,090,542 B2 | 1/2012 | Khvorova et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,440,803 B2 | 5/2013 | Swayze et al. |
| 8,445,666 B2 | 5/2013 | Rigoutsos et al. |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Imanishi et al. |
| 8,709,716 B2 | 4/2014 | Cao et al. |
| 8,828,956 B2 | 9/2014 | Manoharan et al. |
| 9,005,906 B2 | 4/2015 | Swayze et al. |
| 9,012,421 B2 | 4/2015 | Migawa et al. |
| 9,127,276 B2 | 8/2015 | Prakash et al. |
| 9,290,760 B2 | 3/2016 | Rajeev et al. |
| 2001/0053519 A1 | 12/2001 | Fodor et al. |
| 2003/0158403 A1 | 8/2003 | Manoharan et al. |
| 2003/0175906 A1 | 9/2003 | Manoharan et al. |
| 2003/0228597 A1 | 12/2003 | Cowsert et al. |
| 2004/0171570 A1 | 9/2004 | Allerson et al. |
| 2004/0266707 A1 * | 12/2004 | Leake .................. C12N 15/111 514/44 A |
| 2005/0130923 A1 | 6/2005 | Bhat et al. |
| 2005/0244851 A1 | 11/2005 | Blume et al. |
| 2012/0052487 A9 | 11/2005 | Khvorova et al. |
| 2006/0148740 A1 | 7/2006 | Platenburg |
| 2007/0031844 A1 | 2/2007 | Khvorova et al. |
| 2008/0039618 A1 | 2/2008 | Allerson et al. |
| 2010/0190837 A1 | 7/2010 | Migawa et al. |
| 2010/0197762 A1 | 8/2010 | Swayze et al. |
| 2012/0225034 A1 | 9/2012 | Belayew et al. |
| 2013/0130378 A1 | 5/2013 | Manoharan et al. |
| 2013/0288976 A1 | 10/2013 | Van Der Maarel et al. |
| 2014/0107330 A1 | 4/2014 | Freier et al. |
| 2014/0154783 A1 | 6/2014 | Rossomando et al. |
| 2014/0242093 A1 | 8/2014 | Tapscott et al. |
| 2014/0322169 A1 | 10/2014 | Harper et al. |
| 2015/0018540 A1 | 1/2015 | Prakash et al. |
| 2015/0184153 A1 | 7/2015 | Freier et al. |

(56) References Cited

U.S. PATENT DOCUMENTS

| | | |
|---|---|---|
| 2015/0191727 A1 | 7/2015 | Migawa et al. |
| 2015/0267195 A1 | 9/2015 | Seth et al. |
| 2015/0275212 A1 | 10/2015 | Albaek et al. |

OTHER PUBLICATIONS

Branch et al., "A good antisense molecule is hard to find," TIBS (1998) 23:45-50.

Chen et al., "Moipholino-mediated Knockdown of DUX4 Towards Facioscapulohumeral Muscular Dystrophy Therapeutics." Molecular Therapy (2016) 24(8):1405-1411.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Crooke et al., "Basic Principles of Antisense Therapeutics" Antisense Research and Application (1998) Chapter 1:1-50.

FSH Socitey Grant Awards "Contiuing to make progress in understnding and treating FSHD" Feb. 2011.

International Search Report for application No. PCT/US2016/013649 dated May 26, 2016.

New England Biolabs 1998/99 Catalog (cover page and pp. 121 and 284).

Lim et al., "DICER/AGO-dependent epigenetic silencing of D4Z4 repeats enhanced by exogenous siRNA suggests mechanisms and therapies for FSHD" Human Molecular Genetics (2015) 1-12.

Reynolds et al., "Rational siRNA design for RNA interference" Nature Biotechnology (2004) 22(3):326-330.

Sanghvi et al., "Heterocyclic Base Modifications in Nucleic Acids and Their Applications in Antisense Oligonucleotides" Antisense Research and Applications (1993) pp. 273-288.

Tassin et al., "DUX4 expression in FSHD muscle cells: how could such a rare protein cause a myopathy?" J Cell Mod Med (2013) 17(1):76-89.

Crooke et al., "Antisense Drug Technology," Second Edition, CRC Press, 2008, Chapters 1-28; 414 pages.

Egli et al., "Synthesis Improved Antisense Activity and Structural Rationale for the Divergent RNA Affinities of 3'-fluoro Hexitol Nucleic Acid (FHNA and Ara-FHNA) Modified Oligonucleotides," J Am Chem, 2011, 133(41):16642-16649.

Gautschi et al., Activity of a Novel bcl-2/bcl-xLbispecific Antisense Oligonucleotide Against Tumors of Diverse Histologic Origins, J. Natl Cancer Inst., 2001, 93:463-471.

Maher et al., "Comparative Hybrid Arrest by Tandem Antisense Oligodeoxyribonucleotides or Oligodeoxyribonucleoside Methylphosphonates in a Cell-Free System," Nucl. Acid. Res., 1988, 16(8):3341-3358.

Seth et al., "Short Antisense Oligonucleotides with Novel 2'-4—Conformationaly Restricted Nucleoside Analogues Show Improved Potency Without Increased Toxicity in Animals," J Med Chem, 2009, 52:10-13.

Woolf et al., "Specificity of Antisense Oligonucleotides in vivo," PNAS, 1992, 89:7305-7309.

\* cited by examiner

COMPOUNDS AND METHODS FOR MODULATION OF DUX4

STATEMENT OF GOVERNMENT SUPPORT

This invention was made with government support under NS069539 awarded by the National Institutes of Health. The government has certain rights in the invention.

SEQUENCE LISTING

The present application is being filed along with a Sequence Listing in electronic format. The Sequence Listing is provided as a file entitled BIOL0265USASEQ_ST25.txt, created Jun. 27, 2017, which is 24 kb in size. The information in the electronic format of the sequence listing is incorporated herein by reference in its entirety.

BACKGROUND

The present disclosure pertains generally to double-stranded oligonucleotides that modulate gene expression for use in research, diagnostics, and/or therapeutics. One method of modulation of gene expression is RNA interference (RNAi). RNAi generally refers to gene silencing involving the introduction of double-stranded RNA (dsRNA) leading to the sequence-specific reduction of targeted endogenous mRNA levels. The reduction of target mRNA can occur by one of several different mechanisms, depending on the sequence of structure of the dsRNA, such as degradation of the target mRNA or transcriptional silencing in which transcription of the mRNA is inhibited. An additional example of modulation of RNA target function by an occupancy-based mechanism is modulation of microRNA function. MicroRNAs are small non-coding RNAs that regulate the expression of protein-coding RNAs. The binding of an RNAi compound to a microRNA prevents that microRNA from binding to its messenger RNA targets, and thus interferes with the function of the microRNA. Regardless of the specific mechanism, this sequence-specificity makes RNAi compounds extremely attractive as tools for target validation and gene functionalization, as well as therapeutics to selectively modulate the expression of genes involved in the pathogenesis of malignancies and other diseases.

DUX4 is a retrogene encoded in each unit of the D4Z4 macrosatellite repeat array. D4Z4 repeats are bi-directionally transcribed in somatic tissues and generate long stretches of RNA and small RNA fragments that may have a role in epigenetic silencing. Inefficient epigenetic repression of DUX4 in skeletal muscle leads to aberrant expression of the DUX4 protein and facioscapulohumeral dystrophy (FSHD) 1 and 2. FSHD1 and 2 patients exhibit progressive, asymmetric muscle weakness, and there is a need for effective treatment for this disease.

SUMMARY

The present disclosure provides double-stranded small interfering RNA compounds and methods for inhibiting the expression of the DUX4 gene. Certain embodiments are drawn to a method of reducing expression of DUX4 in a cell comprising contacting the cell with a double-stranded small interfering RNA (siRNA) compound targeted to DUX4. In certain embodiments, DUX4 comprises a nucleic acid sequence at least 85% identical to SEQ ID NO:1. In certain embodiments, DUX4 comprises a nucleic acid sequence at least 85% complementary to SEQ ID NO:1. In certain embodiments, DUX4 comprises a nucleic acid sequence at least 90% identical to SEQ ID NO:1. In certain embodiments, DUX4 comprises a nucleic acid sequence at least 95% complementary to SEQ ID NO:1. In certain embodiments, DUX4 comprises a nucleic acid sequence at least 95% identical to SEQ ID NO:1. In certain embodiments, DUX4 comprises a nucleic acid sequence at least 100% complementary to SEQ ID NO:1. In certain embodiments, DUX4 comprises a nucleic acid sequence at least 100% identical to SEQ ID NO:1.

The present disclosure provides the following non-limiting numbered embodiments:

Embodiment 1: A method of inhibiting expression of DUX4 in a cell, comprising contacting a cell with a double-stranded small interfering RNA, and thereby inhibiting expression of DUX4.

Embodiment 2: The method of embodiment 1, wherein the antisense strand of the double-stranded small interfering RNA comprises a nucleic acid sequence at least 85% complementary to SEQ ID NO:1.

Embodiment 3: The method of embodiment 1, wherein the antisense strand of the double-stranded small interfering RNA comprises a nucleic acid sequence at least 90% complementary to SEQ ID NO:1.

Embodiment 4: The method of embodiment 1, wherein the antisense strand of the double-stranded small interfering RNA comprises a nucleic acid sequence at least 95% complementary to SEQ ID NO:1.

Embodiment 5: The method of embodiment 1, wherein the antisense strand of the double-stranded small interfering RNA comprises a nucleic acid sequence 100% complementary to SEQ ID NO:1.

Embodiment 6: The method of any of embodiments 1 to 5, wherein the antisense strand of the double-stranded small interfering RNA comprises a nucleic acid sequence comprising at least 12 contiguous nucleobases of any of the nucleobase sequences of SEQ ID NOs: 15, 17, 21, 23, 27, 33, 35, 37, 39, 41, 43, or 47.

Embodiment 7: The method of any of embodiments 1 to 5, wherein the antisense strand of the double-stranded small interfering RNA comprises a nucleic acid sequence comprising at least 15 contiguous nucleobases of any of the nucleobase sequences of SEQ ID NOs: 15, 17, 21, 23, 27, 33, 35, 37, 39, 41, 43, or 47.

Embodiment 8: The method of any of embodiments 1 to 5, wherein the antisense strand of the double-stranded small interfering RNA comprises a nucleic acid sequence comprising at least 18 contiguous nucleobases of any of the nucleobase sequences of SEQ ID NOs: 15, 17, 21, 23, 27, 33, 35, 37, 39, 41, 43, or 47.

Embodiment 9: The method of any of embodiments 1 to 5, wherein the antisense strand of the double-stranded small interfering RNA comprises a nucleic acid sequence comprising at least 22 contiguous nucleobases of any of the nucleobase sequences of SEQ ID NOs: 15, 17, 21, 23, 27, 33, 35, 37, 39, 41, 43, or 47.

Embodiment 10: The method of any of embodiments 1 to 5, wherein the antisense strand of the double-stranded small interfering RNA consists of the nucleobase sequence of any of SEQ ID NOs: 15, 17, 21, 23, 27, 33, 35, 37, 39, 41, 43, or 47.

Embodiment 11: The method of any of embodiments 1 to 5, wherein the antisense strand of the double-stranded small interfering RNA comprises 16 to 30 linked nucleosides complementary within nucleobases 4295-5840 of SEQ ID NO:1.

Embodiment 12: The method of embodiment 1, wherein the antisense strand of the double-stranded small interfering RNA comprises a nucleic acid sequence at least 85% identical to SEQ ID NO:1.

Embodiment 13: The method of embodiment 1, wherein the antisense strand of the double-stranded small interfering RNA comprises a nucleic acid sequence at least 90% identical to SEQ ID NO:1.

Embodiment 14: The method of embodiment 1, wherein the antisense strand of the double-stranded small interfering RNA comprises a nucleic acid sequence at least 95% identical to SEQ ID NO:1.

Embodiment 15: The method of embodiment 1, wherein the antisense strand of the double-stranded small interfering RNA comprises a nucleic acid sequence at least 100% identical to SEQ ID NO:1.

Embodiment 16: The method of any of embodiments 12 to 15, wherein the antisense strand of the double-stranded small interfering RNA comprises a nucleic acid sequence comprising at least 12 contiguous nucleobases of any of the nucleobase sequences of SEQ ID NOs: 45, 49, 51, 53, or 55.

Embodiment 17: The method of any of embodiments 12 to 15, wherein the antisense strand of the double-stranded small interfering RNA comprises a nucleic acid sequence comprising at least 15 contiguous nucleobases of any of the nucleobase sequences of SEQ ID NOs: 45, 49, 51, 53, or 55.

Embodiment 18: The method of any of embodiments 12 to 15, wherein the antisense strand of the double-stranded small interfering RNA comprises a nucleic acid sequence comprising at least 18 contiguous nucleobases of any of the nucleobase sequences of SEQ ID NOs: 45, 49, 51, 53, or 55.

Embodiment 19: The method of any of embodiments 12 to 15, wherein the antisense strand of the double-stranded small interfering RNA comprises a nucleic acid sequence comprising at least 22 contiguous nucleobases of any of the nucleobase sequences of SEQ ID NOs: 45, 49, 51, 53, or 55.

Embodiment 20: The method of any of embodiments 12 to 15, wherein the antisense strand of the double-stranded small interfering RNA consists of the nucleobase sequence of any of SEQ ID NOs: 45, 49, 51, 53, or 55.

Embodiment 21: The method of any of embodiments 1 to 20, wherein the sense strand of the double-stranded small interfering RNA comprises a nucleic acid sequence at least 85% complementary to the antisense strand of the double-stranded small interfering RNA.

Embodiment 22: The method of any of embodiments 1 to 20, wherein the sense strand of the double-stranded small interfering RNA comprises a nucleic acid sequence at least 90% complementary to the antisense strand of the double-stranded small interfering RNA.

Embodiment 23: The method of any of embodiments 1 to 20, wherein the sense strand of the double-stranded small interfering RNA comprises a nucleic acid sequence at least 95% complementary to the antisense strand of the double-stranded small interfering RNA.

Embodiment 24: The method of any of embodiments 1 to 20, wherein the sense strand of the double-stranded small interfering RNA comprises a nucleic acid sequence 100% complementary to the antisense strand of the double-stranded small interfering RNA.

Embodiment 25: The method of any of embodiments 1 to 24, wherein the sense strand of the double-stranded small interfering RNA comprises at least 1 modified nucleoside.

Embodiment 26: The method of embodiment 25, wherein each nucleoside of the sense strand of the double-stranded small interfering RNA comprises a modified nucleoside.

Embodiment 27: The method of embodiment 25 or 26, wherein the modified nucleoside is selected from a 2'-F modified nucleoside or a 2'-OMe modified nucleoside.

Embodiment 28: The method of any of embodiments 1 to 27, wherein the sense strand of the double-stranded small interfering RNA comprises at least 1 modified internucleoside linkage.

Embodiment 29: The method of any of embodiments 1 to 27, wherein the sense strand of the double-stranded small interfering RNA comprises at least 5 modified internucleoside linkages.

Embodiment 30: The method of embodiments 28 or 29, wherein each modified internucleoside linkage is a phosphorothioate internucleoside linkage.

Embodiment 31: The method of any of embodiments 1 to 30, wherein the cell is in vitro.

Embodiment 32: The method of any of embodiments 1 to 30, wherein the cell is in an animal.

Embodiment 33: The method of embodiment 32, wherein the animal is a human.

Embodiment 34: The method of any of embodiments 1-33, wherein expression of DUX4 is inhibited by at least 10%.

Embodiment 35: The method of any of embodiments 1-33, wherein expression of DUX4 is inhibited by at least 20%.

Embodiment 36: The method of any of embodiments 1-33, wherein expression of DUX4 is inhibited by at least 30%.

Embodiment 37: The method of any of embodiments 1-33, wherein expression of DUX4 is inhibited by at least 40%.

Embodiment 38: The method of any of embodiments 1-33, wherein expression of DUX4 is inhibited by at least 50%.

Embodiment 39: The method of any of embodiments 1-33, wherein expression of DUX4 is inhibited by at least 60%.

Embodiment 40: The method of any of embodiments 1-33, wherein expression of DUX4 is inhibited by at least 70%.

Embodiment 41: The method of any of embodiments 1-33, wherein expression of DUX4 is inhibited by at least 80%.

Embodiment 42: A double-stranded small interfering RNA, wherein the antisense strand of the double-stranded small interfering RNA comprises a nucleic acid sequence comprising at least 12 contiguous nucleobases of any of the nucleobase sequences of SEQ ID NOs: 15, 17, 21, 23, 27, 33, 35, 37, 39, 41, 43, or 47.

Embodiment 43: The double-stranded small interfering RNA of embodiment 42, wherein the antisense strand of the double-stranded small interfering RNA comprises a nucleic acid sequence comprising at least 15 contiguous nucleobases of any of the nucleobase sequences of SEQ ID NOs: 15, 17, 21, 23, 27, 33, 35, 37, 39, 41, 43, or 47.

Embodiment 44: The double-stranded small interfering RNA of embodiment 42, wherein the antisense strand of the double-stranded small interfering RNA comprises a nucleic acid sequence comprising at least 18 contiguous nucleobases of any of the nucleobase sequences of SEQ ID NOs: 15, 17, 21, 23, 27, 33, 35, 37, 39, 41, 43, or 47.

Embodiment 45: The double-stranded small interfering RNA of embodiment 42, wherein the antisense strand of the double-stranded small interfering RNA comprises a nucleic acid sequence comprising at least 22 contiguous nucleobases of any of the nucleobase sequences of SEQ ID NOs: 15, 17, 21, 23, 27, 33, 35, 37, 39, 41, 43, or 47.

Embodiment 46: The double-stranded small interfering RNA of embodiment 42, wherein the antisense strand of the double-stranded small interfering RNA consists of the nucleobase sequence of any of SEQ ID NOs: 15, 17, 21, 23, 27, 33, 35, 37, 39, 41, 43, or 47.

Embodiment 47: The double-stranded small interfering RNA of any of embodiments 42 to 46, wherein the antisense strand of the double-stranded small interfering RNA comprises a nucleic acid sequence at least 85% complementary to SEQ ID NO:1.

Embodiment 48: The double-stranded small interfering RNA of any of embodiments 42 to 46, wherein the antisense strand of the double-stranded small interfering RNA comprises a nucleic acid sequence at least 90% complementary to SEQ ID NO:1.

Embodiment 49: The double-stranded small interfering RNA of any of embodiments 42 to 46, wherein the antisense strand of the double-stranded small interfering RNA comprises a nucleic acid sequence at least 95% complementary to SEQ ID NO:1.

Embodiment 50: The double-stranded small interfering RNA of any of embodiments 42 to 46, wherein the antisense strand of the double-stranded small interfering RNA comprises a nucleic acid sequence 100% complementary to SEQ ID NO:1.

Embodiment 51: A double-stranded small interfering RNA, wherein the antisense strand of the double-stranded small interfering RNA comprises a nucleic acid sequence, wherein the antisense strand of the double-stranded small interfering RNA comprises a nucleic acid sequence at least 100% identical to SEQ ID NO: 1.

Embodiment 52: A double-stranded small interfering RNA, wherein the antisense strand of the double-stranded small interfering RNA comprises a nucleic acid sequence comprising at least 12 contiguous nucleobases of any of the nucleobase sequences of SEQ ID NOs: 45, 49, 51, 53, or 55.

Embodiment 53: The double-stranded small interfering RNA of embodiment 52, wherein the antisense strand of the double-stranded small interfering RNA comprises a nucleic acid sequence comprising at least 15 contiguous nucleobases of any of the nucleobase sequences of SEQ ID NOs: 45, 49, 51, 53, or 55.

Embodiment 54: The double-stranded small interfering RNA of embodiment 52, wherein the antisense strand of the double-stranded small interfering RNA comprises a nucleic acid sequence comprising at least 18 contiguous nucleobases of any of the nucleobase sequences of SEQ ID NOs: 45, 49, 51, 53, or 55.

Embodiment 55: The double-stranded small interfering RNA of embodiment 52, wherein the antisense strand of the double-stranded small interfering RNA comprises a nucleic acid sequence comprising at least 22 contiguous nucleobases of any of the nucleobase sequences of SEQ ID NOs: 45, 49, 51, 53, or 55.

Embodiment 56: The double-stranded small interfering RNA of embodiment 52, wherein the antisense strand of the double-stranded small interfering RNA consists of the nucleobase sequence of any of SEQ ID NOs: 45, 49, 51, 53, or 55.

Embodiment 57: The double-stranded small interfering RNA of any of embodiments 42 to 56, wherein the sense strand of the double-stranded small interfering RNA comprises a nucleic acid sequence at least 85% complementary to the antisense strand of the double-stranded small interfering RNA.

Embodiment 58: The double-stranded small interfering RNA of any of embodiments 42 to 56, wherein the sense strand of the double-stranded small interfering RNA comprises a nucleic acid sequence at least 90% complementary to the antisense strand of the double-stranded small interfering RNA.

Embodiment 59: The double-stranded small interfering RNA of any of embodiments 42 to 56, wherein the sense strand of the double-stranded small interfering RNA comprises a nucleic acid sequence at least 95% complementary to the antisense strand of the double-stranded small interfering RNA.

Embodiment 60: The double-stranded small interfering RNA of any of embodiments 42 to 56, wherein the sense strand of the double-stranded small interfering RNA comprises a nucleic acid sequence 100% complementary to the antisense strand of the double-stranded small interfering RNA.

Embodiment 61: The double-stranded small interfering RNA of any of embodiments 42 to 60, wherein the sense strand of the double-stranded small interfering RNA comprises at least 1 modified nucleoside.

Embodiment 62: The double-stranded small interfering RNA of embodiment 61, wherein each nucleoside of the sense strand of the double-stranded small interfering RNA comprises a modified nucleoside.

Embodiment 63: The double-stranded small interfering RNA of embodiment 61 or 62, wherein the modified nucleoside is selected from a 2'-F modified nucleoside or a 2'-OMe modified nucleoside.

Embodiment 64: The double-stranded small interfering RNA of any of embodiments 42 to 63, wherein the sense strand of the double-stranded small interfering RNA comprises at least 1 modified internucleoside linkage.

Embodiment 65: The double-stranded small interfering RNA of any of embodiments 42 to 63, wherein the sense strand of the double-stranded small interfering RNA comprises at least 5 modified internucleoside linkages.

Embodiment 66: The double-stranded small interfering RNA of embodiments 64 or 65, wherein each modified internucleoside linkage is a phosphorothioate internucleoside linkage.

Embodiment 67: The double-stranded small interfering RNA of any of embodiments 42 to 66, comprising a conjugate.

Embodiment 68: A pharmaceutical composition comprising the double-stranded small interfering RNA of any of embodiments 42 to 67 or a salt thereof, and at least one pharmaceutically acceptable diluent or carrier.

Embodiment 69: A method of treating facioscapulohumeral muscular dystrophy comprising administering the double-stranded small interfering RNA of any of embodiments 42 to 68 to a subject in need thereof.

Embodiment 70: Use of the double-stranded small interfering RNA of any of embodiments 42 to 68 for the treatment of facioscapulohumeral muscular dystrophy.

Embodiment 71: Use of the double-stranded small interfering RNA of any of embodiments 42 to 68 for the preparation of a medicament for the treatment of facioscapulohumeral muscular dystrophy.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

It is understood that the sequence set forth in each SEQ ID NO described herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

"DUX4" means any nucleic acid or protein of DUX4. "DUX4 nucleic acid" means any nucleic acid encoding DUX4 protein. In certain embodiments, DUX4 nucleic acid comprises GENBANK Accession No. FJ439133.1, SEQ ID NO: 1. For example, in certain embodiments, a DUX4 nucleic acid includes a DNA sequence encoding DUX4, an RNA sequence transcribed from DNA encoding DUX4 (including genomic DNA comprising introns and exons), including a non-protein encoding (i.e. non-coding) RNA sequence, and an mRNA sequence encoding DUX4.

"Double-stranded small interfering RNA" means any duplex RNA structure comprising two anti-parallel and substantially complementary nucleic acid strands. In certain embodiments, Double-stranded small interfering RNA comprise a sense strand and an antisense strand, wherein the antisense strand is complementary to a target nucleic acid.

"Complementarity" means the capacity for pairing between nucleobases of a first nucleic acid and a second nucleic acid.

"Contiguous nucleobases" means nucleobases immediately adjacent to each other.

"Deoxyribonucleotide" means a nucleotide having a hydrogen at the 2' position of the sugar portion of the nucleotide. Deoxyribonucleotides may be modified with any of a variety of substituents.

"Expression" includes all the functions by which a gene's coded information is converted into structures present and operating in a cell. Such structures include, but are not limited to the products of transcription and translation.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Inhibiting the expression or activity" refers to a reduction or blockade of the expression or activity and does not necessarily indicate a total elimination of expression or activity.

"Internucleoside linkage" refers to the chemical bond between nucleosides.

"Linked nucleosides" means adjacent nucleosides linked together by an internucleoside linkage.

"Modified internucleoside linkage" refers to a substitution or any change from a naturally occurring internucleoside bond (i.e. a phosphodiester internucleoside bond).

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C) and uracil (U).

"Modified nucleoside" means a nucleoside having, independently, a modified sugar moiety and/or modified nucleobase.

"Modified nucleotide" means a nucleotide having, independently, a modified sugar moiety, modified internucleoside linkage, or modified nucleobase.

"Modified sugar" means substitution and/or any change from a natural sugar moiety. In certain embodiments modified sugars include 2'-F modified sugars and 2'-OMe modified sugars.

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

"Nucleobase sequence" means the order of contiguous nucleobases independent of any sugar, linkage, and/or nucleobase modification.

"Nucleoside" means a nucleobase linked to a sugar.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Sites," as used herein, are defined as unique nucleobase positions within a target nucleic acid.

"Subject" means a human or non-human animal selected for treatment or therapy.

"Target gene" refers to a gene encoding a target.

"Target nucleic acid" refers to a nucleic acid, the modulation of which is desired.

Double-stranded Small Interfering RNA (siRNA) Compounds

In certain embodiments, compounds disclosed herein are double-stranded small interfering RNA (siRNA) compounds. In certain embodiments, compounds disclosed herein are double-stranded RNAi compounds (siRNA). In certain embodiments, siRNA compounds may comprise unmodified RNA nucleosides, but modified internucleoside linkages. In certain embodiments, siRNA compounds may comprise unmodified DNA nucleosides, but modified internucleoside linkages.

Several embodiments relate to double-stranded compositions wherein each strand comprises a motif defined by the location of one or more modified or unmodified nucleosides. In certain embodiments, compositions are provided comprising a first and a second oligomeric compound that are fully or at least partially hybridized to form a duplex region and further comprising a region that is complementary to and hybridizes to a nucleic acid target. It is suitable that such a composition comprise a first oligomeric compound that is an antisense strand having full or partial complementarity to a nucleic acid target and a second oligomeric compound that is a sense strand having one or more regions of complementarity to and forming at least one duplex region with the first oligomeric compound.

The compositions of several embodiments modulate gene expression by hybridizing to a nucleic acid target resulting in loss of its normal function. In certain embodiment, the degradation of the target nucleic acid is facilitated by an activated RISC complex that is formed with compositions of the invention.

Several embodiments are directed to double-stranded compositions wherein one of the strands is useful in, for example, influencing the preferential loading of the opposite strand into the RISC (or cleavage) complex. The compositions are useful for targeting selected nucleic acid molecules and modulating the expression of one or more genes. In some embodiments, the compositions of the present invention hybridize to a portion of a target RNA resulting in loss of normal function of the target RNA.

Certain embodiments are drawn to double-stranded compositions wherein both the strands comprises a hemimer motif, a fully modified motif, a positionally modified motif or an alternating motif. Each strand of the compositions of the present invention can be modified to fulfil a particular role in for example the siRNA pathway. Using a different motif in each strand or the same motif with different chemical modifications in each strand permits targeting the antisense strand for the RISC complex while inhibiting the incorporation of the sense strand. Within this model, each strand can be independently modified such that it is enhanced for its particular role. The antisense strand can be modified at the 5'-end to enhance its role in one region of the RISC while the 3'-end can be modified differentially to enhance its role in a different region of the RISC.

The double-stranded oligonucleotide molecules can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The double-stranded oligonucleotide molecules can be assembled from two separate oligonucleotides, where one strand is the sense strand and the other is the antisense strand, wherein the antisense and sense strands are self-complementary (i.e. each strand comprises nucleotide sequence that is complementary to nucleotide sequence in the other strand; such as where the antisense strand and sense strand form a duplex or double-stranded structure, for example wherein the double-stranded region is about 15 to about 30, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 to about 25 or more nucleotides of the double-stranded oligonucleotide molecule are complementary to the target nucleic acid or a portion thereof). Alternatively, the double-stranded oligonucleotide is assembled from a single oligonucleotide, where the self-complementary sense and antisense regions of the siRNA are linked by means of a nucleic acid based or non-nucleic acid-based linker(s).

The double-stranded oligonucleotide can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The double-stranded oligonucleotide can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNAi.

In certain embodiments, the double-stranded oligonucleotide comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic interactions, and/or stacking interactions. In certain embodiments, the double-stranded oligonucleotide comprises nucleotide sequence that is complementary to nucleotide sequence of a target gene. In another embodiment, the double-stranded oligonucleotide interacts with nucleotide sequence of a target gene in a manner that causes inhibition of expression of the target gene.

As used herein, double-stranded oligonucleotides need not be limited to those molecules containing only RNA, but further encompasses chemically modified nucleotides and non-nucleotides. In certain embodiments, the short interfering nucleic acid molecules lack 2'-hydroxy (2'-OH) containing nucleotides. In certain embodiments short interfering nucleic acids optionally do not include any ribonucleotides (e.g., nucleotides having a 2'-OH group). Such double-stranded oligonucleotides that do not require the presence of ribonucleotides within the molecule to support RNAi can however have an attached linker or linkers or other attached or associated groups, moieties, or chains containing one or more nucleotides with 2'-OH groups. Optionally, double-stranded oligonucleotides can comprise ribonucleotides at about 5, 10, 20, 30, 40, or 50% of the nucleotide positions. As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, double-stranded oligonucleotides can be used to epigenetically silence genes at both the post-transcriptional level and the pre-transcriptional level. In a non-limiting example, epigenetic regulation of gene expression by siRNA molecules of the invention can result from siRNA mediated modification of chromatin structure or methylation pattern to alter gene expression (see, for example, Verdel et al., 2004, Science, 303, 672-676; Pal-Bhadra et al., 2004, Science, 303, 669-672; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

It is contemplated that compounds and compositions of several embodiments provided herein can target by a dsRNA-mediated gene silencing or RNAi mechanism, including, e.g., "hairpin" or stem-loop double-stranded RNA effector molecules in which a single RNA strand with self-complementary sequences is capable of assuming a double-stranded conformation, or duplex dsRNA effector molecules comprising two separate strands of RNA. In various embodiments, the dsRNA consists entirely of ribonucleotides or consists of a mixture of ribonucleotides and deoxynucleotides, such as the RNA/DNA hybrids disclosed, for example, by WO 00/63364, filed Apr. 19, 2000, or U.S. Ser. No. 60/130,377, filed Apr. 21, 1999. The dsRNA or dsRNA effector molecule may be a single molecule with a region of self-complementarity such that nucleotides in one segment of the molecule base pair with nucleotides in another segment of the molecule. In various embodiments, a dsRNA that consists of a single molecule consists entirely of ribonucleotides or includes a region of ribonucleotides that is complementary to a region of deoxyribonucleotides. Alternatively, the dsRNA may include two different strands that have a region of complementarity to each other.

In various embodiments, both strands consist entirely of ribonucleotides, one strand consists entirely of ribonucleotides and one strand consists entirely of deoxyribonucleotides, or one or both strands contain a mixture of ribonucleotides and deoxyribonucleotides. In certain embodiments, the regions of complementarity are at least 70, 80, 90, 95, 98, or 100% complementary to each other and to a target nucleic acid sequence. In certain embodiments, the region of the dsRNA that is present in a double-stranded conformation includes at least 19, 20, 21, 22, 23, 24, 25, 26, 27, 28, 29, 30, 50, 75, 100, 200, 500, 1000, 2000 or 5000 nucleotides or includes all of the nucleotides in a cDNA or other target nucleic acid sequence being represented in the dsRNA. In some embodiments, the dsRNA does not contain any single stranded regions, such as single stranded ends, or the dsRNA is a hairpin. In other embodiments, the dsRNA has one or more single stranded regions or overhangs. In certain embodiments, RNA/DNA hybrids include a DNA strand or region that is an antisense strand or region (e.g, has at least 70, 80, 90, 95, 98, or 100% complementarity to a target nucleic acid) and an RNA strand or region that is a sense strand or region (e.g, has at least 70, 80, 90, 95, 98, or 100% identity to a target nucleic acid), and vice versa.

In various embodiments, the RNA/DNA hybrid is made in vitro using enzymatic or chemical synthetic methods such as those described herein or those described in WO 00/63364, filed Apr. 19, 2000, or U.S. Ser. No. 60/130,377, filed Apr. 21, 1999. In other embodiments, a DNA strand synthesized in vitro is complexed with an RNA strand made in vivo or in vitro before, after, or concurrent with the transformation of the DNA strand into the cell. In yet other embodiments, the dsRNA is a single circular nucleic acid containing a sense and an antisense region, or the dsRNA includes a circular nucleic acid and either a second circular nucleic acid or a linear nucleic acid (see, for example, WO 00/63364, filed Apr. 19, 2000, or U.S. Ser. No. 60/130,377, filed Apr. 21, 1999.) Exemplary circular nucleic acids include lariat structures in which the free 5' phosphoryl group of a nucleotide becomes linked to the 2' hydroxyl group of another nucleotide in a loop back fashion.

In other embodiments, the dsRNA includes one or more modified nucleotides in which the 2' position in the sugar contains a halogen (such as fluorine group) or contains an alkoxy group (such as a methoxy group) which increases the half-life of the dsRNA in vitro or in vivo compared to the corresponding dsRNA in which the corresponding 2' position contains a hydrogen or an hydroxyl group. In yet other embodiments, the dsRNA includes one or more linkages between adjacent nucleotides other than a naturally-occurring phosphodiester linkage. Examples of such linkages include phosphoramide, phosphorothioate, and phosphorodithioate linkages. The dsRNAs may also be chemically modified nucleic acid molecules as taught in U.S. Pat. No. 6,673,661. In other embodiments, the dsRNA contains one or two capped strands, as disclosed, for example, by WO 00/63364, filed Apr. 19, 2000, or U.S. Ser. No. 60/130,377, filed Apr. 21, 1999.

In other embodiments, the dsRNA can be any of the at least partially dsRNA molecules disclosed in WO 00/63364, as well as any of the dsRNA molecules described in U.S. Provisional Application 60/399,998; and U.S. Provisional Application 60/419,532, and PCT/US2003/033466, the teaching of which is hereby incorporated by reference. Any of the dsRNAs may be expressed in vitro or in vivo using the methods described herein or standard methods, such as those described in WO 00/63364.

Certain Embodiments

Certain embodiments are drawn to a method of reducing expression of DUX4 in a cell comprising contacting the cell with a double-stranded small interfering RNA compound targeted to DUX4. In certain embodiments, DUX4 comprises a nucleic acid sequence at least 85% identical to SEQ ID NO:1. In certain embodiments, DUX4 comprises a nucleic acid sequence at least 85% complementary to SEQ ID NO:1.

DUX4 is a retrogene encoded in each unit of the D4Z4 macrosatellite repeat array. D4Z4 repeats are bi-directionally transcribed in somatic tissues and generate long stretches of RNA and small RNA fragments. In certain embodiments, these D4Z4 repeats serve to in epigenetically silence DUX4. Most people have around 200 D4Z4 repeats, enough repeats to keep DUX4 repressed, however, when fewer repeats are presents (e.g. 10 or fewer repeats) in addition to the small genetic change on Chromosome 4 called a haplotype polymorphism, DUX4 will express itself. The inefficient epigenetic repression of DUX4 in skeletal muscle leads to aberrant expression of the DUX4 protein and facioscapulohumeral dystrophy (FSHD) 1 and 2. FSHD1 and 2 patients exhibit progressive, asymmetric muscle weakness, and there is a need for effective treatment for this disease. Therefore, in certain embodiments it is desirable to inhibit expression of DUX4. In certain embodiments it is desirable to inhibit expression of DUX4 in a subject having 10 or fewer D4Z4 repeats.

In certain embodiments, DUX4 expression is inhibited by contacting a cell with a double-stranded small interfering RNA compound. In certain embodiments, DUX4 expression is inhibited by contacting a cell with a double-stranded small interfering RNA compound disclosed herein.

Certain Pharmaceutical Compositions

In certain embodiments, the present invention provides pharmaceutical compositions comprising one or more the double-stranded small interfering RNA compounds. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, the double-stranded small interfering RNA compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising the double-stranded small interfering RNA compounds encompass any pharmaceutically acceptable salts, esters, or salts of such esters. In certain embodiments, pharmaceutical compositions comprising the double-stranded small interfering RNA compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of the double-stranded small interfering RNA compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an the double-stranded small interfering RNA compound which are cleaved by endogenous nucleases within the body, to form the active antisense oligomeric compound.

Lipid moieties have been used in nucleic acid therapies in a variety of methods. In certain such methods, the the double-stranded small interfering RNA is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more the double-stranded small interfering RNA compounds and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition provided herein comprises a the double-stranded small interfering RNA in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more the double-stranded small interfering RNA compounds provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, the present invention provides compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human.

In certain embodiments, the present invention provides methods of administering a pharmaceutical composition comprising a double-stranded small interfering RNA compound of the present disclosure to an animal. Suitable administration routes include, but are not limited to, oral, rectal, transmucosal, intestinal, enteral, topical, suppository, through inhalation, intrathecal, intracerebroventricular, intraperitoneal, intranasal, intratumoral, and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., into the ears).

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified or naturally occurring bases, such as "AT$^{me}$CGAUCG," wherein $^{me}$C indicates a cytosine base comprising a methyl group at the 5-position.

EXAMPLES

The following examples illustrate certain embodiments of the present invention and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1: Silencing of DUX4 with siRNA Targeting the Promoter Region and Coding Region Double-stranded small interfering RNA (siRNA) targeting the human DUX4 promoter region and coding region were made and tested for inhibition of target transcript expression in vitro. Their sequences are listed in the table below. The guide, or antisense, strand of each duplex is indicated by "as". The passenger, or sense, strand of each duplex is indicated by "s". Each siRNA listed in the table below is targeted to the sense strand of human genomic DUX4 sequence (GENBANK Accession No. FJ439133.1, SEQ ID NO: 1) "Start" indicates the 5'-most nucleoside to which the siRNA is targeted in the genomic DUX4 sequence. "Stop" indicates the 3'-most nucleoside to which the siRNA is targeted in the genomic DUX4 sequence. The name of each siRNA is the position on SEQ ID NO: 1 that the siRNA targets relative to the transcriptional start site (TSS), which is position 5852 of SEQ ID NO: 1. For example, the "−30" siRNA targets SEQ ID NO: 1 thirty nucleotides upstream of the TSS, at position 5822 of SEQ ID NO: 1.

TABLE 1 siRNA duplexes targeting human DUX4

| Name | Sequence (5' to 3') | Start site | Stop site | SEQ ID No. |
|---|---|---|---|---|
| −1558 as | TGGGCTGGTGGAGAGGCAG | 4295 | 4313 | 13 |
| −1558 s | CTGCCTCTCCACCAGCCCA | | | 14 |
| −1247 as | TTCCTCTCTCCATCTCTGC | 4606 | 4624 | 15 |
| −1247 s | GCAGAGATGGAGAGAGGAA | | | 16 |
| −921 as | TTGTCCCGGAGGAAACCGC | 4932 | 4950 | 17 |
| −921 s | GCGGTTTCCTCCGGGACAA | | | 18 |
| −779 as | AATCACGCCTCCGTCGTCC | 5074 | 5092 | 19 |
| −779 s | GGACGACGGAGGCGTGATT | | | 20 |
| −657 as | TTCCCTGCATGTTTCCGGGTGCCCG | 5195 | 5219 | 21 |
| −657 s | CGGGCACCCGGAAACATGCAGGGAA | | | 22 |
| −650 as | CTTCCCTGCATGTTTCCGG | 5202 | 5220 | 23 |
| −650 s | CCGGAAACATGCAGGGAAG | | | 24 |
| −476 as | TGTGGCTCTCGTTCATTTC | 5376 | 5394 | 25 |
| −476 s | GAAATGAACGAGAGCCACA | | | 26 |
| −385 as | CTCCGTGGGAGTCTTGAGTGTGCCA | 5467 | 5491 | 27 |
| −385 s | TGGCACACTCAAGACTCCCACGGAG | | | 28 |
| −368 as | TGGAACTGAACCTCCGTGG | 5484 | 5502 | 29 |
| −368 s | CCACGGAGGTTCAGTTCCA | | | 30 |
| −131 as | TGGTGGTGGTGGTGGTGGT | 5721 | 5739 | 31 |
| −131 s | ACCACCACCACCACCACCA | | | 32 |
| −37 as | CACCCCTTCATGAATGGCG | 5815 | 5833 | 33 |
| −37 s | CGCCATTCATGAAGGGGTG | | | 34 |
| −30 as | CAGGCTCCACCCCTTCATG | 5822 | 5840 | 35 |
| −30 s | CATGAAGGGGTGGAGCCTG | | | 36 |
| +258 as | TTCCGCTCAAAGCAGGCTC | 6109 | 6127 | 37 |
| +258 s | GAGCCTGCTTTGAGCGGAA | | | 38 |
| +484 as | AAAGCGATCCTTCTCAAAGGCTCGG | 6335 | 6359 | 39 |
| +484 s | CCGAGCCTTTGAGAAGGATCGCTTT | | | 40 |
| +614 as | CCTGCGCGGGCGCCCTGCC | 6465 | 6483 | 41 |
| +614 s | GGCAGGGCGCCCGCGCAGG | | | 42 |
| +2176 as | TATCTCTGAACTAATCATC | 8026 | 8044 | 43 |
| +2176 s | GATGATTAGTTCAGAGATA | | | 44 |

Primary myoblasts (MB) obtained from FSHD1 or FSHD2 patients were cultured in growth media (F-10 Medium, 20% fetal bovine serum, 10 ng/ml hFGF, 1 µM Dexamethasone) without antibiotics in 6-well plates at approximately 50% confluency 24 hours before transfection. The cells were transfected with 5 µL Lipofectamine RNAiMAX (Life Technologies, Carlsbad, Calif.) and 100 pmol of a siRNA listed in the table above or a control siRNA that does not target DUX4. 48 hours after the transfection, the cells were treated with differentiation media (DMEM, 1% heat-inactivated horse serum, 10 µg/mL transferrin, and 10 µg/mLinsulin) to induce differentiation into myotubes (MT). An additional 48 hours later, cells were harvested and total RNA was isolated using TRIZOL (Life Technologies) according to the manufacturer's directions. Two DNase reactions were performed, and the purified RNA was tested for genomic DNA contamination by PCR and gel electrophoresis.

RT-PCR was performed on the isolated RNA to generate and amplify DUX4 cDNA using Superscript II and OligodT primer (Life Technologies), forward PCR primer: GGCCCGGTGAGAGACTCCACA (SEQ ID NO: 2) or GAGCTCCTGGCGAGCCCGGAGTTTCTG (SEQ ID NO: 3), and reverse PCR primer: CCAGGAGATGTAACTCTAATCCAGGTTTGC (SEQ ID NO: 4). RT-PCR was also performed on TIMM17b, as a control, using forward PCR primer: GGAGCCTTCACTATGGGTGT (SEQ ID NO: 5) and reverse PCR primer: CACAGCATTGGCACTACCTC (SEQ ID NO: 6). The resulting cDNA were separated on a 1% agarose gel, which was qualitatively analyzed visually. The results are shown in the table below as percent expression relative to the expression in cells that were transfected with the control siRNA.

Selected siRNAs that exhibited silencing of DUX4 using the method described above were further tested for silencing of DUX4 and inhibition of ZSCAN4 expression, a gene that is upregulated by DUX4. Quantitative RT-PCR was performed using an automated ABI 7900 PCR machine (Applied Biosystems) using Fast Start SYBR Green Master Mix (Roche) with ROX passive reference dye added. GAPDH was used as the normalization control. The PCR primers used for ZSCAN4 were: forward primer: TGGAAATCAAGTGGCAAAAA (SEQ ID NO: 7) and reverse primer: CTGCATGTGGACGTGGAC (SEQ ID NO: 8). The PCR primers used for GAPDH were: forward primer: GTGAAGGTCGGAGTCAAC (SEQ ID NO: 9) and reverse primer: TGAGGTCAATGAAGGGGTC (SEQ ID NO: 10). The DUX4 primers were: forward primer: GGCCCGGTGAGAGACTCCACA (SEQ ID NO: 2) and reverse PCR primer: CCAGGAGATGTAACTCTAATCCAGGTTTGC (SEQ ID NO: 4). The results for DUX4 and ZSCAN4 normalized to GAPDH are shown in the table below as percent expression relative to the expression in cells that were transfected with the control siRNA. A result of "n/a" indicates that the corresponding experiment was not performed. The results show that several siRNAs targeting the promoter and coding regions of DUX4 silenced mRNA expression of DUX4 and of a DUX4 target, ZSCAN4.

TABLE 2

DUX4 and ZSCAN4 transcript levels following siRNA treatment

| siRNA Name | DUX4 RT-PCR | DUX4 RT-qPCR | ZSCAN4 RT-qPCR |
|---|---|---|---|
| control | 100% | 100% | 100% |
| −1558 | ≤50% | n/a | n/a |
| −1247 | >50% | n/a | n/a |
| −921 | >50% | n/a | n/a |
| −779 | >50% | n/a | n/a |
| −657 | ≤50% | 16.35% | 3.81% |
| −650 | ≤50% | 13.18% | 8.55% |
| −476 | ≤50% | 11.52% | 1.30% |
| −385 | ≤50% | 10.14% | 10.06% |
| −368 | >50% | n/a | n/a |
| −131 | >50% | n/a | n/a |

TABLE 2-continued

DUX4 and ZSCAN4 transcript levels following siRNA treatment

| siRNA Name | DUX4 RT-PCR | DUX4 RT-qPCR | ZSCAN4 RT-qPCR |
|---|---|---|---|
| −37 | ≤50% | n/a | n/a |
| −30 | >50% | n/a | n/a |
| +258 | ≤50% | 11.80% | 3.51% |
| +484 | ≤50% | 2.66% | 0.276% |
| +614 | >50% | n/a | n/a |
| +2176 | ≤50% | n/a | n/a |

Example 2: Time Course of Silencing of DUX4 with siRNA

The effects of siRNA targeting DUX4 (see Table 1) on expression of DUX4 and DUX4 target RFPL2 over time were tested in FSHD2 muscle cells. Primary myoblasts were transfected as described in Example 1. Cells were differentiated 48 hours prior to harvest and transfected 12, 24, or 96 hours prior to harvest, as listed in Table 3 below. Thus, cells harvested at the 12 and 24 hours post-transfection had already undergone differentiation to myotubes by the time of transfection, whereas cells harvested at 96 hours post-transfection underwent differentiation 48 hours after transfection. RNA was isolated and analyzed by qRT-PCR, as described in Example 1. Primers used for RFPL2 were: forward primer: CCCACATCAAGGAACTGGAG (SEQ ID NO: 11) and reverse primer: TGTTGGCATCCAAGGTCATA (SEQ ID NO: 12). The results for DUX4 and RFPL2 normalized to GAPDH are shown in Table 3 below as percent expression relative to the expression in cells that were transfected with the control siRNA. The results show that the siRNAs targeting the DUX4 mRNA inhibited DUX4 and RFPL2 expression by 24 hours, whereas the siRNAs targeting the DUX4 promoter region exhibited delayed kinetics with DUX4 and RFPL2 silencing observed by 4 days post-transfection.

TABLE 3

Time course of DUX4 and RFPL2 expression following siRNA treatment

| siRNA Name | Time (h post-transfection) | DUX4 RT-qPCR | RFPL2 RT-qPCR |
|---|---|---|---|
| −657 | 12 | 93.96% | 94.48% |
|  | 24 | 101.52% | 123.60% |
|  | 96 | 23.03% | 23.20% |
| −650 | 12 | 86.96% | 101.03% |
|  | 24 | 97.56% | 114.51% |
|  | 96 | 14.13% | 13.50% |
| −385 | 12 | 108.17% | 108.22% |
|  | 24 | 73.79% | 110.91% |
|  | 96 | 26.47% | 15.01% |
| +258 | 12 | 67.67% | 92.34% |
|  | 24 | 35.25% | 34.29% |
|  | 96 | 10.17% | 3.78% |
| +484 | 12 | 69.08% | 108.87% |
|  | 24 | 28.71% | 29.42% |
|  | 96 | 9.34% | 2.05% |

Example 3: Silencing of DUX4 with Antisense Targeting siRNA siRNAs targeting the complement of SEQ ID NO: 1 (antisense targeting siRNA) were made and tested for inhibition of DUX4 transcript expression in vitro. Antisense targeting siRNAs are marked with an "*" in Table 4 below. All other sequences listed in Table 4 target SEQ ID NO: 1 (sense targeting). The guide, or antisense, strand of each duplex is indicated by "as". The passenger, or sense, strand of each duplex is indicated by "s". The start and stop sites listed for the antisense targeting siRNAs in Table 4 indicate the 3'-most and 5'-most nucleosides, respectively, of SEQ ID NO: 1 that are complementary to the sense strand ("s") of each antisense targeting siRNA. Primary FSHD2 myoblasts were transfected as described in Example 1 with an siRNA listed in Table 4 below. RNA was isolated and analyzed by qRT-PCR, as described in Example 1. The results for DUX4 expression normalized to GAPDH are shown in Table 4 below as percent expression relative to the expression in cells that were transfected with the control siRNA. The results show that some antisense targeting siRNAs inhibited DUX4 expression.

TABLE 4

Antisense targeting siRNA effects on DUX4

| Name | | Sequence (5' to 3') | Start site | Stop site | DUX4 RT-qPCR | SEQ ID No. |
|---|---|---|---|---|---|---|
| −1301* | as | AGCGCCTGGCGGCGGAACGCAGACC | 4551 | 4527 | 23.41% | 45 |
| −1301* | s | GGTCTGCGTTCCGCCGCCAGGCGCT |  |  |  | 46 |
| −1263 | as | ATCTCTGCCCGCCTTCCCTCCCGCC | 4589 | 4613 | 118.86% | 47 |
| −1263 | s | GGCGGGAGGGAAGGCGGGCAGAGAT |  |  |  | 48 |
| −657 | as | TTCCCTGCATGTTTCCGGGTGCCCG | 5195 | 5219 | 17.60% | 21 |
| −657 | s | CGGGCACCCGGAAACATGCAGGGAA |  |  |  | 22 |
| −623* | as | GAAACATGCAGGGAAGGGTGCAAGC | 5229 | 5205 | 89.67% | 49 |
| −623* | s | GCTTGCACCCTTCCCTGCATGTTTC |  |  |  | 50 |
| −385 | as | CTCCGTGGGAGTCTTGAGTGTGCCA | 5467 | 5491 | 26.84% | 27 |
| −385 | s | TGGCACACTCAAGACTCCCACGGAG |  |  |  | 28 |
| −351* | as | AAGACTCCCACGGAGGTTCAGTTCC | 5501 | 5477 | 99.11% | 51 |
| −351* | s | GGAACTGAACCTCCGTGGGAGTCTT |  |  |  | 52 |
| +93* | as | TGCACAGTCCGGCTGAGGTGCACGG | 5944 | 5920 | 20.96% | 53 |
| +93* | s | CCGTGCACCTCAGCCGGACTGTGCA |  |  |  | 54 |
| +484 | as | AAAGCGATCCTTCTCAAAGGCTCGG | 6335 | 6359 | 5.99% | 39 |
| +484 | s | CCGAGCCTTTGAGAAGGATCGCTTT |  |  |  | 40 |
| +519* | as | AGAAGGATCGCTTTCCAGGCATCGC | 6370 | 6346 | 27.39% | 55 |
| +519* | s | GCGATGCCTGGAAAGCGATCCTTCT |  |  |  | 56 |

The invention claimed is:

1. A double-stranded small interfering RNA, comprising a sense strand and an antisense strand, wherein the antisense strand of the double-stranded small interfering RNA has a nucleobase sequence complementary to at least 12 contiguous nucleobases of:
   an equal length portion of nucleobases 5,195-5,220 of SEQ ID NO: 1;
   an equal length portion of nucleobases 5,467-5,491 of SEQ ID NO: 1; or
   an equal length portion of nucleobases 5,815-5,840 of SEQ ID NO: 1; and
   wherein said sense strand is at least 85% complementary to said antisense strand;
   wherein said sense strand is at least 85% identical to an equal length portion of SEQ ID NO:1; and
   wherein said sense strand comprises at least one modified nucleoside.

2. The double-stranded small interfering RNA of claim 1, wherein at least one nucleoside of the sense strand of the double-stranded small interfering RNA comprises a modified sugar.

3. The double-stranded small interfering RNA of claim 2, wherein each nucleoside of the sense strand of the double-stranded small interfering RNA comprises a modified sugar.

4. The double-stranded small interfering RNA of claim 3, wherein each modified sugar is independently selected from a 2'-F modified sugar or a 2'-OMe modified sugar.

5. The double-stranded small interfering RNA of claim 1, wherein the sense strand of the double-stranded small interfering RNA comprises at least 1 modified internucleoside linkage.

6. The double-stranded small interfering RNA of claim 5, wherein the sense strand of the double-stranded small interfering RNA comprises at least 5 modified internucleoside linkages.

7. The double-stranded small interfering RNA of claim 5, wherein each modified internucleoside linkage is a phosphorothioate internucleoside linkage.

8. A double-stranded small interfering RNA, comprising a sense strand and an antisense strand, wherein the antisense strand of the double-stranded small interfering RNA has a nucleobase sequence comprising at least 12 contiguous nucleobases of any of the nucleobase sequences of SEQ ID NOs: 13, 21, 23, 27, 33, 39, or 43; and wherein said sense strand is at least 85% complementary to said antisense strand, wherein said antisense strand is at least 85% complementary to SEQ ID NO: 1, and wherein said sense strand comprises at least one modified nucleoside.

9. The double-stranded small interfering RNA of claim 8, wherein at least one nucleoside of the sense strand of the double-stranded small interfering RNA comprises a modified sugar.

10. The double-stranded small interfering RNA of claim 9, wherein each nucleoside of the sense strand of the double-stranded small interfering RNA comprises a modified sugar.

11. The double-stranded small interfering RNA of claim 10, wherein each modified sugar is independently selected from a 2'-F modified sugar or a 2'-OMe modified sugar.

12. The double-stranded small interfering RNA of claim 8, wherein the sense strand of the double-stranded small interfering RNA comprises at least 1 modified internucleoside linkage.

13. The double-stranded small interfering RNA of claim 12, wherein the sense strand of the double-stranded small interfering RNA comprises at least 5 modified internucleoside linkages.

14. The double-stranded small interfering RNA of claim 13, wherein each modified internucleoside linkage is a phosphorothioate internucleoside linkage.

15. A pharmaceutical composition comprising the double-stranded small interfering RNA of claim 1 and at least one pharmaceutically acceptable diluent or carrier.

16. The double-stranded small interfering RNA of claim 2, wherein the modified sugar is a 2'-F modified sugar or a 2'-OMe modified sugar.

17. The double-stranded small interfering RNA of claim 9, wherein the modified sugar is a 2'-F modified sugar or a 2'-OMe modified sugar.

* * * * *

SEQUENCE LISTING

<160> NUMBER OF SEQ ID NOS: 56

<210> SEQ ID NO 1
<211> LENGTH: 8671
<212> TYPE: DNA
<213> ORGANISM: Homo sapiens

<400> SEQUENCE: 1

| | | | | | |
|---|---|---|---|---|---|
| gggatgcgcg | cgcctggggc | tctcccacag | ggggctttcg | tgagccaggc | agcgagggcc | 60 |
| gcccccgcgc | tgcagcccag | ccaggccgcg | acggcagagg | gggtctccca | acctgccccg | 120 |
| gcgcgcgggg | atttcgccta | cgccgccccg | gctcctccgg | acggggcgct | ctcccaccct | 180 |
| caggctcctc | ggtggcctcc | gcacccgggc | aaaagccggg | aggaccggga | cccgcagcgc | 240 |
| gacggcctgc | cgggcccctg | cgcggtggca | cagcctgggc | ccgctcaagc | ggggccgcag | 300 |
| ggccaagggg | tgcttgcgcc | acccacgtcc | caggggagtc | cgtggtgggg | ctggggccgg | 360 |
| ggtccccagg | tcgccggggc | ggcgtgggaa | ccccaagccg | gggcagctcc | acctccccag | 420 |
| cccgcgcccc | cggacgcctc | cgcgcggcag | gggcagatgc | aaggcatccc | ggcgccctcc | 480 |
| caggcgctcc | aggagccggc | gccctggtct | gcactcccct | gcggcctgct | gctggatgag | 540 |
| ctcctggcga | gcccggagtt | tctgcagcag | gcgcaacctc | tcctagaaac | ggaggccccg | 600 |
| ggggagctgg | aggcctcgga | agaggccgcc | tcgctggaag | caccctcag | cgaggaagaa | 660 |
| taccgggctc | tgctggagga | gctttaggac | gcggggttgg | gacggggtcg | ggtggttcgg | 720 |
| ggcagggcgg | tggcctctct | ttcgcgggga | acgcctggct | ggctacggag | gggcgtgtct | 780 |
| ccgccccgcc | ccctccaccg | ggctgaccgg | cctgggattc | ctgccttcta | ggtctaggcc | 840 |
| cggtgagaga | ctccacaccg | cggagaactg | ccattctttc | ctgggcatcc | cggggatccc | 900 |
| agagccggcc | caggtaccag | caggtgggcc | gcctactgcg | cacgcgcggg | tttgcgggca | 960 |
| gccgcctggg | ctgtgggagc | agcccgggca | gagctctcct | gcctctccac | cagcccaccc | 1020 |
| cgccgcctga | ccgccccctc | cccacccca | cccccaccc | ccggaaaacg | cgtcgtcccc | 1080 |
| tgggctgggt | ggagaccccc | gtcccgcgaa | acaccgggcc | ccgcgcagcg | tccgggcctg | 1140 |
| acaccgctcc | ggcggctcgc | ctcctctgcg | ccccgcgcc | accgtcgccc | gccgcccgg | 1200 |
| gcccctgcag | ccgcccaggt | gccagcacgg | agcgcctggc | ggcggaacgc | agaccccagg | 1260 |
| cccggcgcac | accggggacg | ctgagcgttc | caggcgggag | ggaaggcggg | cagagatgga | 1320 |
| gagaggaacg | ggagacctag | aggggcggaa | ggacgggcgg | agggacgtta | ggagggaggg | 1380 |
| agggaggcag | ggaggcaggg | aggaacggag | ggaaagacag | agcgacgcag | ggactggggg | 1440 |
| cgggcgggag | ggagccgggg | acggacgggg | ggaggaaggc | agggaggaaa | agcggtcctc | 1500 |
| ggcctccggg | agtagcggga | ccccgccct | ccgggaaaac | ggtcagcgtc | cggcgcgggc | 1560 |
| tgagggctgg | gccacagcc | gccgcgccgg | ccggcgcggc | acccattcgc | cccggttccg | 1620 |
| tggcccaggg | agtgggcggt | ttcctccggg | acaaaagacc | gggactcggg | ttgccgtcgg | 1680 |
| gttttcaccc | gcgcggttca | cagaccgcac | atcccaggc | tgagccctgc | aacgcggcgc | 1740 |
| gaggccgaca | gccccggcca | cggaggagcc | acacgcagga | cgacggaggc | gtgatttttgg | 1800 |
| tttccgcgtg | gctttgccct | ccgcaaggcg | gcctgttgct | cacgtctctc | cggccccga | 1860 |
| aaggctggcc | atgccgactg | tttgctcccg | gagctctgcg | ggcacccgga | aacatgcagg | 1920 |
| gaagggtgca | agccggcat | ggtgccttcg | ctctccttgc | caggttccaa | accggccaca | 1980 |
| ctgcagactc | cccacgttgc | cgcacgcggg | aatccatcgt | caggccatca | cgccggggag | 2040 |
| gcatctcctc | tctggggtct | cgctctggtc | ttctacgtgg | aaatgaacga | gagccacacg | 2100 |

```
cctgcgtgtg cgagaccgtc ccggcaacgg cgacgcccac aggcattgcc tccttcacgg    2160
agagagggcc tggcacactc aagactccca cggaggttca gttccacact cccctccacc    2220
ctcccaggct ggtttctccc tgctgccgac gcgtgggagc ccagagagcg gcttcccgtt    2280
cccgcgggat ccctggagag gtccggagag ccggcccccg aaacgcgccc ccctcccccc    2340
tcccccctct ccccgttcct cttcgtctct ccggcccac caccaccacc gccaccacgc     2400
cctcccccac cacccccccc ccccccacca ccaccaccac caccccgccg gccggccca    2460 ggcctcgacg ccctgggtcc cttccggggt ggggcgggct gtcccagggg ggctcaccgc    2520
cattcatgaa ggggtggagc ctgcctgcct gtgggccttt acaagggcgg ctggctgggt    2580
ggctggctgt ccgggcaggc cccctggctg cacctgccgc agtgcacagt ccggctgagg    2640
tgcacgggag cccgccggcc tctctctgcc cgcgtccgtc cgtgaaattc cggccggggc    2700
tcaccgcgat ggccctcccg acaccctcgg acagcaccct ccccgcggaa gcccggggac    2760
gaggacggcg acggagactc gtttggaccc cgagccaaag cgaggccctg cgagcctgct    2820
ttgagcggaa cccgtacccg ggcatcgcca ccagagaacg gctggcccag gccatcggca    2880
ttccggagcc cagggtccag atttggtttc agaatgagag gtcacgccag ctgaggcagc    2940
accggcggga atctcggccc tggcccggga gacgcggccc gccagaaggc cggcgaaagc    3000
ggaccgccgt caccggatcc cagaccgccc tgctcctccg agcctttgag aaggatcgct    3060
ttccaggcat cgccgcccgg gaggagctgg ccagagagac gggcctcccg gagtccagga    3120
ttcagatctg gtttcagaat cgaagggcca ggcacccggg acagggtggc agggcgcccg    3180
cgcaggcagg cggcctgtgc agcgcggccc ccggcggggg tcaccctgct ccctcgtggg    3240
tcgccttcgc ccacaccggc gcgtggggaa cggggcttcc cgcaccccac gtgccctgcg    3300
cgcctggggc tctcccacag ggggcttcg tgagccaggc agcgagggcc gccccgcgc     3360 tgcagcccag ccaggccgcg ccggcagagg ggatctccca acctgccccg gcgcgcgggg    3420
atttggccta cgccgccccg gctcctccgg acggggcgct ctcccaccct caggctcctc    3480
ggtggcctcc gcacccgggc aaaagccggg aggaccggga cccgcagcgc gacggcctgc    3540
cgggcccctg cgcggtggca cagcctgggc ccgctcaagc ggggccgcag ggccaagggg    3600
tgcttgcgcc acccacgtcc caggggagtc cgtggtgggg ctgggccgg ggtccccagg     3660 tcgccggggc ggcgtgggaa ccccaagccg gggcagctcc acctcccag cccgcgcccc     3720 cggacgcctc cgcctccgcg cggcaggggc agatgcaagg catcccggcg ccctcccagg    3780
cgctccagga gccggcgccc tggtctgcac tcccctgcgg cctgctgctg gatgagctcc    3840
tggcgagccc ggagtttctg cagcaggcgc aacctctcct agaaacggag gccccggggg    3900
agctggaggc ctcggaagag gccgcctcgc tggaagcacc cctcagcgag gaagaatacc    3960
gggctctgct ggaggagctt taggacgcgg ggttgggacg gggtcgggtg gttcggggca    4020
gggcggtggc ctctcttcg cggggaacac ctggctggct acggaggggc gtgtctccgc     4080 cccgcccct ccaccgggct gaccggcctg ggattcctgc cttctaggtc taggcccggt     4140
gagagactcc acaccgcgga gaactgccat tctttcctgg gcatcccggg gatcccagag    4200
ccggcccagt accagcagg tgggccgcct actgcgcacg cgcgggtttg cgggcagccg     4260
cctgggctgt gggagcagcc cggcagagc tcctgcct ctccaccagc ccaccccgcc      4320
gcctgaccgc cccctcccca cccccacccc ccaccccgg aaaacgcgtc gtccctggg     4380 ctgggtggag accccgtcc cgcgaaacac cgggcccgc gcagcgtccg ggcctgacac     4440
cgctccggcg gctcgcctcc tctgcgcccc cgcgccaccg tcgcccgccc gcccgggccc    4500
```

```
ctgcagccgc ccaggtgcca gcacggagcg cctggcggcg aacgcagac cccaggcccg      4560 gcgcacaccg gggacgctga gcgttccagg cgggagggaa ggcgggcaga gatggagaga      4620
ggaacgggag acctagaggg gcggaaggac gggcggaggg acgttaggag ggagggaggg      4680
aggcagggag gcagggagga acggagggaa agacagagcg acgcagggac tggggcgggg      4740
cgggagggag ccgggggacg gggggaggaa ggcagggagg aaaagcggtc ctcggcctcc      4800
gggagtagcg ggaccccgc cctccgggaa aacggtcagc gtccggcgcg ggctgagggc       4860
tgggcccaca gccgccgcgc cggccggcgg ggcaccaccc attcgccccg gttccggggc      4920
ccagggagtg ggcggtttcc tccgggacaa aagaccggga ctcgggttgc cgtcgggtct      4980
tcacccgcgc ggttcacaga ccgcacatcc ccaggctcag ccctgcaacg cggcgcgagg      5040
ccgacagccc cggccacgga ggagccacac gcaggacgac ggaggcgtga ttttggtttc      5100
cgcgtggctt tgccctccgc aaggcggcct gttgctcacg tctctccggc ccccgaaagg      5160
ctggccatgc cgactgtttg ctcccggagc tctgcgggca cccggaaaca tgcagggaag      5220
ggtgcaagcc cggcacggtg ccttcgctct ccttgccagg ttccaaaccg gccacactgc      5280
agactcccca cgttgccgca cgcgggaatc catcgtcagg ccatcacgcc ggggaggcat      5340
ctcctctctg gggtctcgct ctggtcttct acgtggaaat gaacgagagc cacacgcctg      5400
cgtgtgcgag accgtcccgg caacggcgac gcccacaggc attgcctcct tcacggagag      5460
agggcctggc acactcaaga ctcccacgga ggttcagttc cacactcccc tccaccctcc      5520
caggctggtt tctccctgct gccgacgcgt gggagcccag agagcggctt cccgttcccg      5580
cgggatccct ggagaggtcc ggagagccgg ccccgaaac gcgccccct cccccctccc        5640 ccctctcccc cttcctcttc gtctctccgg ccccaccacc accaccgcca ccacgccctc      5700
cccccccacc cccccccccc accaccacca ccaccaccac ccgcggcc ggccccaggc        5760 ctcgacgccc tgggtcccct ccggggtggg gcgggctgtc ccaggggggc tcaccgccat      5820
tcatgaaggg gtgagcctg cctgctgtg ggcctttaca agggcggctg gctggctggc         5880
tggctgtccg ggcaggcctc ctggctgcac ctgccgcagt gcacagtccg gctgaggtgc      5940
acggagcccc gccggcctct ctctgcccgc gtccgtccgt gaaattccgg ccggggctca      6000
ccgcgatggc cctcccgaca ccctcggaca gcaccctccc cgcggaagcc cggggacgag      6060
gacggcgacg gagactcgtt tggaccccga gccaaagcga ggccctgcga gcctgctttg      6120
agcggaaccc gtaccgggc atcgccacca gagaacggct ggcccaggcc atcggcattc       6180
cggagcccag ggtccagatt tggtttcaga atgagaggtc acgccagctg aggcagcacc      6240
ggcgggaatc tcggccctgg cccgggagac gcggcccgcc agaaggccgg cgaaagcgga      6300
ccgccgtcac cggatcccag accgccctgc tcctccgagc cttttgagaag gatcgctttc      6360 caggcatcgc cgcccgggag gagctggcca gagagacggg cctcccggag tccaggattc      6420
agatctggtt tcagaatcga agggccaggc accggggaca gggtggcagg gcgcccgcgc      6480
aggcaggcgg cctgtgcagc gcggccccg gcggggtca ccctgctccc tcgtgggtcg        6540
ccttcgccca caccggcgcg tgggaacgg ggcttcccgc accccacgtg ccctgcgcgc       6600
ctggggctct cccacagggg gctttcgtga ccaggcagc gagggccgcc ccgcgctgc        6660 agcccagcca ggccgcgccg gcagagggga tctcccaacc tgccccggcg cgcggggatt      6720
tcgcctacgc cgccccggct cctccggacg gggcgctctc ccaccctcag gctcctcgct      6780
ggcctccgca cccgggcaaa agccgggagg accgggaccc gcagcgcgac ggcctgccgg      6840
gccccgctgc ggtggcacag cctgggcccg ctcaagcggg gccgcagggc caaggggtgc     6900
```

| | |
|---|---|
| ttgcgccacc cacgtcccag gggagtccgt ggtggggctg gggccggggt ccccaggtcg | 6960 |
| ccggggcggc gtgggaaccc caagccgggg cagctccacc tccccagccc gcgccccgg | 7020 |
| acgcctccgc ctccgcgcgg caggggcaga tgcaaggcat cccggcgccc tcccaggcgc | 7080 |
| tccaggagcc ggcgccctgg tctgcactcc cctgcggcct gctgctggat gagctcctgg | 7140 |
| cgagcccgga gtttctgcag caggcgcaac ctctcctaga aacggaggcc ccggggagc | 7200 |
| tggaggcctc ggaagaggcc gcctcgctgg aagcacccct cagcgaggaa gaataccggg | 7260 |
| ctctgctgga ggagctttag gacgcggggt tgggacgggg tcgggtggtt cggggcaggg | 7320 |
| ccgtggcctc tctttcgcgg ggaacacctg gctggctacg gaggggcgtg tctccgcccc | 7380 |
| gcccctcca ccgggctgac cggcctggga ttcctgcctt ctaggtctag gcccggtgag | 7440 |
| agactccaca ccgcggagaa ctgccattct ttcctgggca tcccggggat cccagagccg | 7500 |
| gcccaggtac cagcaggtgg gccgcctact gcgcacgcgc gggtttgcgg gcagccgcct | 7560 |
| gggctgtggg agcagcccgg gcagagctct cctgcctctc caccagccca ccccgccgcc | 7620 |
| tgaccgcccc ctccccaccc ccacccccca ccccggaaa acgcgtcgtc ccctgggctg | 7680 |
| ggtggagacc cccgtcccgc gaaacaccgg gcccgcgca gcgtccgggc ctgacaccgc | 7740 |
| tccggcggct cgcctcctct gcgccccgc gccaccgtcg cccgcccgcc cgggcccctg | 7800 |
| cagcctccca gctgccagcg cggagctcct ggcggtcaaa agcataccctc tgtctgtctt | 7860 |
| tgcccgcttc ctggctagac ctgcgcgcag tgcgcacccc ggctgacgtg caagggagct | 7920 |
| cgctggcctc tctgtgccct tgttcttccg tgaaattctg gctgaatgtc tccccccacc | 7980 |
| ttccgacgct gtctaggcaa acctggatta gagttacatc tcctggatga ttagttcaga | 8040 |
| gatatattaa aatgccccct ccctgtggat cctatagaag atttgcatct tttgtgtgat | 8100 |
| gagtgcagag atatgtcaca atatcccctg tagaaaaagc ctgaaattgg tttacataac | 8160 |
| ttcggtgatc agtgcagatg tgtttcagaa ctccatagta gactgaacct agagaatggt | 8220 |
| tacatcactt aggtgatcag tgtagagata tgttaaaatt ctcgtgtaga cagagcctag | 8280 |
| acaattgtta catcacctag tgatcagtgc agggataagt cataaagcct cctgtaggca | 8340 |
| gagtgtaggc aagtgttccc tccctgggct gatcagtgca gagatatctc acaaagcccc | 8400 |
| tataagccaa accttgacaa gggttacatc acctgtttga gcagtggaaa tatatatcac | 8460 |
| aaagcccct gtagacaaag cccagacaat ttttacatct cctgagtgag cattggagag | 8520 |
| atctgtcaca atgcccctgt aggcagagct tagacaagtg ttacatcacc tgggtgatca | 8580 |
| gtgcagagat atgtcaaaac gctcctgtag tctgaaccta gacaggagtt acatcacctt | 8640 |
| ggggatcagt gcagagatac gtgagaattc c | 8671 |

<210> SEQ ID NO 2
<211> LENGTH: 21
<212> TYPE: DNA
<213> ORGANISM: Artificial sequence
<220> FEATURE:
<223> OTHER INFORMATION: Primer

<400> SEQUENCE: 2

| | |
|---|---|
| ggcccggtga gagactccac a | 21 |

<210> SEQ ID NO 3
<211> LENGTH: 27
<212> TYPE: DNA
<213> ORGANISM: Artificial sequence
<220> FEATURE:
<223> OTHER INFORMATION: Primer

<400> SEQUENCE: 3
gagctcctgg cgagcccgga gtttctg                                27

<210> SEQ ID NO 4
<211> LENGTH: 30
<212> TYPE: DNA
<213> ORGANISM: Artificial sequence
<220> FEATURE:
<223> OTHER INFORMATION: Primer

<400> SEQUENCE: 4
ccaggagatg taactctaat ccaggtttgc                             30

<210> SEQ ID NO 5
<211> LENGTH: 20
<212> TYPE: DNA
<213> ORGANISM: Artificial sequence
<220> FEATURE:
<223> OTHER INFORMATION: Primer

<400> SEQUENCE: 5
ggagccttca ctatgggtgt                                        20

<210> SEQ ID NO 6
<211> LENGTH: 20
<212> TYPE: DNA
<213> ORGANISM: Artificial sequence
<220> FEATURE:
<223> OTHER INFORMATION: Primer

<400> SEQUENCE: 6
cacagcattg gcactacctc                                        20

<210> SEQ ID NO 7
<211> LENGTH: 20
<212> TYPE: DNA
<213> ORGANISM: Artificial sequence
<220> FEATURE:
<223> OTHER INFORMATION: Primer

<400> SEQUENCE: 7
tggaaatcaa gtggcaaaaa                                        20

<210> SEQ ID NO 8
<211> LENGTH: 18
<212> TYPE: DNA
<213> ORGANISM: Artificial sequence
<220> FEATURE:
<223> OTHER INFORMATION: Primer

<400> SEQUENCE: 8
ctgcatgtgg acgtggac                                          18

<210> SEQ ID NO 9
<211> LENGTH: 18
<212> TYPE: DNA
<213> ORGANISM: Artificial sequence
<220> FEATURE:
<223> OTHER INFORMATION: Primer

<400> SEQUENCE: 9
gtgaaggtcg gagtcaac                                          18

```
<210> SEQ ID NO 10
<211> LENGTH: 19
<212> TYPE: DNA
<213> ORGANISM: Artificial sequence
<220> FEATURE:
<223> OTHER INFORMATION: Primer

<400> SEQUENCE: 10
tgaggtcaat gaaggggtc                                                  19

<210> SEQ ID NO 11
<211> LENGTH: 20
<212> TYPE: DNA
<213> ORGANISM: Artificial sequence
<220> FEATURE:
<223> OTHER INFORMATION: Primer

<400> SEQUENCE: 11
cccacatcaa ggaactggag                                                 20

<210> SEQ ID NO 12
<211> LENGTH: 20
<212> TYPE: DNA
<213> ORGANISM: Artificial sequence
<220> FEATURE:
<223> OTHER INFORMATION: Primer

<400> SEQUENCE: 12
tgttggcatc caaggtcata                                                 20

<210> SEQ ID NO 13
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 13
tgggctggtg gagaggcag                                                  19

<210> SEQ ID NO 14
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 14
ctgcctctcc accagccca                                                  19

<210> SEQ ID NO 15
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 15
ttcctctctc catctctgc                                                  19

<210> SEQ ID NO 16
<211> LENGTH: 19
<212> TYPE: DNA
<213> ORGANISM: Artificial sequence
<220> FEATURE:
<223> OTHER INFORMATION: Synthetic oligonucleotide
```

<400> SEQUENCE: 16
gcagagatgg agagaggaa                                              19

<210> SEQ ID NO 17
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 17
ttgtcccgga ggaaaccgc                                              19

<210> SEQ ID NO 18
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 18
gcggtttcct ccgggacaa                                              19

<210> SEQ ID NO 19
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 19
aatcacgcct ccgtcgtcc                                              19

<210> SEQ ID NO 20
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 20
ggacgacgga ggcgtgatt                                              19

<210> SEQ ID NO 21
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 21
ttccctgcat gtttccgggt gcccg                                       25

<210> SEQ ID NO 22
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 22
cgggcacccg gaaacatgca gggaa                                       25

<210> SEQ ID NO 23
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 23
cttccctgca tgtttccgg        19

<210> SEQ ID NO 24
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 24
ccggaaacat gcagggaag        19

<210> SEQ ID NO 25
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 25
tgtggctctc gttcatttc        19

<210> SEQ ID NO 26
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 26
gaaatgaacg agagccaca        19

<210> SEQ ID NO 27
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 27
ctccgtggga gtcttgagtg tgcca        25

<210> SEQ ID NO 28
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 28
tggcacactc aagactccca cggag        25

<210> SEQ ID NO 29
<211> LENGTH: 19
<212> TYPE: DNA
<213> ORGANISM: Artificial sequence
<220> FEATURE:
<223> OTHER INFORMATION: Synthetic oligonucleotide

```
<400> SEQUENCE: 29
tggaactgaa cctccgtgg                                               19

<210> SEQ ID NO 30
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 30
ccacggaggt tcagttcca                                               19

<210> SEQ ID NO 31
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 31
tggtggtggt ggtggtggt                                               19

<210> SEQ ID NO 32
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 32
accaccacca ccaccacca                                               19

<210> SEQ ID NO 33
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 33
caccccttca tgaatggcg                                               19

<210> SEQ ID NO 34
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 34
cgccattcat gaaggggtg                                               19

<210> SEQ ID NO 35
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 35
caggctccac cccttcatg                                               19
```

```
<210> SEQ ID NO 36
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 36
catgaagggg tggagcctg                                                19

<210> SEQ ID NO 37
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 37
ttccgctcaa agcaggctc                                                19

<210> SEQ ID NO 38
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 38
gagcctgctt tgagcggaa                                                19

<210> SEQ ID NO 39
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 39
aaagcgatcc ttctcaaagg ctcgg                                         25

<210> SEQ ID NO 40
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 40
ccgagccttt gagaaggatc gcttt                                         25

<210> SEQ ID NO 41
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 41
cctgcgcggg cgccctgcc                                                19

<210> SEQ ID NO 42
<211> LENGTH: 19
<212> TYPE: DNA
<213> ORGANISM: Artificial sequence
<220> FEATURE:
<223> OTHER INFORMATION: Synthetic oligonucleotide
```

<400> SEQUENCE: 42
ggcagggcgc ccgcgcagg                                        19

<210> SEQ ID NO 43
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 43
tatctctgaa ctaatcatc                                        19

<210> SEQ ID NO 44
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 44
gatgattagt tcagagata                                        19

<210> SEQ ID NO 45
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 45
agcgcctggc ggcggaacgc agacc                                 25

<210> SEQ ID NO 46
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 46
ggtctgcgtt ccgccgccag gcgct                                 25

<210> SEQ ID NO 47
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 47
atctctgccc gccttccctc ccgcc                                 25

<210> SEQ ID NO 48
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 48
ggcgggaggg aaggcgggca gagat                                 25

```
<210> SEQ ID NO 49
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 49
gaaacatgca gggaagggtg caagc                                              25

<210> SEQ ID NO 50
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 50
gcttgcaccc ttccctgcat gtttc                                              25

<210> SEQ ID NO 51
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 51
aagactccca cggaggttca gttcc                                              25

<210> SEQ ID NO 52
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 52
ggaactgaac ctccgtggga gtctt                                              25

<210> SEQ ID NO 53
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 53
tgcacagtcc ggctgaggtg cacgg                                              25

<210> SEQ ID NO 54
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 54
ccgtgcacct cagccggact gtgca                                              25

<210> SEQ ID NO 55
<211> LENGTH: 25
<212> TYPE: DNA
<213> ORGANISM: Artificial sequence
<220> FEATURE:
<223> OTHER INFORMATION: Synthetic oligonucleotide
```

```
<400> SEQUENCE: 55
agaaggatcg ctttccaggc atcgc                                             25

<210> SEQ ID NO 56
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 56
gcgatgcctg gaaagcgatc cttct                                             25
```